United States Patent
Karrer et al.

[11] 3,998,891
[45] Dec. 21, 1976

[54] PHENOXYPHENYLALKYLTHIO-, ALKENYLTHIO-, ALKINYLTHIO- AND BENZYLTHIO-ALKOXY ETHERS

[75] Inventors: Friedrich Karrer, Basel; Saleem Farooq, Aesch, both of Switzerland

[73] Assignee: Ciba-Geigy Corporation, Ardsley, N.Y.

[22] Filed: Apr. 19, 1976

[21] Appl. No.: 677,996

Related U.S. Application Data

[62] Division of Ser. No. 569,040, April 17, 1975, Pat. No. 3,963,786.

[30] Foreign Application Priority Data

Apr. 18, 1974 Switzerland .................. 5364/74
Mar. 12, 1975 Switzerland .................. 3123/75

[52] U.S. Cl. .......................................... 260/609 F
[51] Int. Cl.² .................................... C07C 149/32
[58] Field of Search .............................. 260/609 F

[56] References Cited

UNITED STATES PATENTS 3,155,733  11/1964  Reifschneider ............... 260/609 F

FOREIGN PATENTS OR APPLICATIONS 667,891  4/1966  Belgium ........................ 260/609 F

*Primary Examiner*—Lewis Gotts
*Assistant Examiner*—D. R. Phillips
*Attorney, Agent, or Firm*—Frederick H. Rabin

[57] ABSTRACT

New phenoxy-phenyl ethers, their manufacture and use for the control of insects and representatives of the order acarina are disclosed. The compounds correspond to the formula

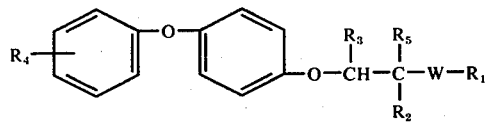

wherein
W represents —O—, —S—,
$R_1$ represents $C_1$–$C_6$-alkyl, $C_3$–$C_6$-cycloalkyl or $C_5$–$C_6$-cycloalkenyl, $C_2$–$C_4$-haloalkenyl, $C_3$–$C_5$-alkynyl, $C_2$–$C_4$-alkenyl or benzyl,
$R_2$ represents hydrogen, methyl or ethyl,
$R_3$ represents hydrogen or methyl, or
$R_2$ and $R_3$ together with the chain represent a 5- or 6-membered saturated ring, and
$R_4$ and $R_5$ each represent hydrogen or methyl.

2 Claims, No Drawings

PHENOXYPHENYLALKYLTHIO-, ALKENYLTHIO-, ALKINYLTHIO- AND BENZYLTHIO-ALKOXY ETHERS

This is a division of application Ser. No. 569,040 filed Apr. 17, 1975, now U.S. Pat. No. 3,963,786.

The present invention relates to phenoxy-phenylethers, to processes for their production and to their use in pest control.

The phenoxy-phenyl ethers have the formula

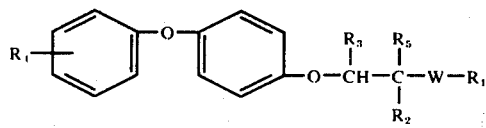

wherein

W represents $-O-$, $-S-$, $R_1$ represents $C_1-C_6$-alkyl, $C_3-C_6$-cycloalkyl or $C_5-C_6$-cycloalkenyl, $C_2-C_4$-haloalkenyl, $C_3-C_5$-alkynyl, $C_2-C_4$-alkenyl or benzyl, $R_2$ represents hydrogen, methyl or ethyl, $R_3$ represents hydrogen or methyl, or $R_2$ and $R_3$ together with the chain represent a 5- or 6-membered saturated ring, and $R_4$ and $R_5$ each represent hydrogen or methyl.

The alkyl, alkenyl or alkynyl groups denoted by $R_1$ can be straight-chain or branched chain. Examples of such groups are, inter alia: methyl, ethyl, propyl, isopropyl, n-, i-, sec.-, tert.-butyl, n-pentyl and n-hexyl and isomers thereof, vinyl, allyl, methallyl, propargyl, 3-methyl-2-butenyl or 3-methyl-2-pentenyl.

Compounds of formula I preferred on account of their action are those wherein

W represents $-O-$, $-S-$, $R_1$ represents $C_1-C_6$-alkyl, $C_3-C_6$-cycloalkyl, $C_3-C_4$-akynyl, $C_2-C_4$-alkenyl or $C_3-C_4$-chloroalkenyl, $R_2$ represents hydrogen or methyl, and $R_3$, $R_4$ and $R_5$ represent hydrogen.

Compounds of formula I likewise exhibiting a good action are those wherein

W represents $-O-$, $R_1$ represents methyl, ethyl, isopropyl, isobutyl, sec.-butyl, allyl or propargyl, $R_2$ represents hydrogen or methyl, and $R_3$, $R_4$ and $R_5$ each represent hydrogen.

The compounds of formula I can be produced by, for example, the following methods known per se:

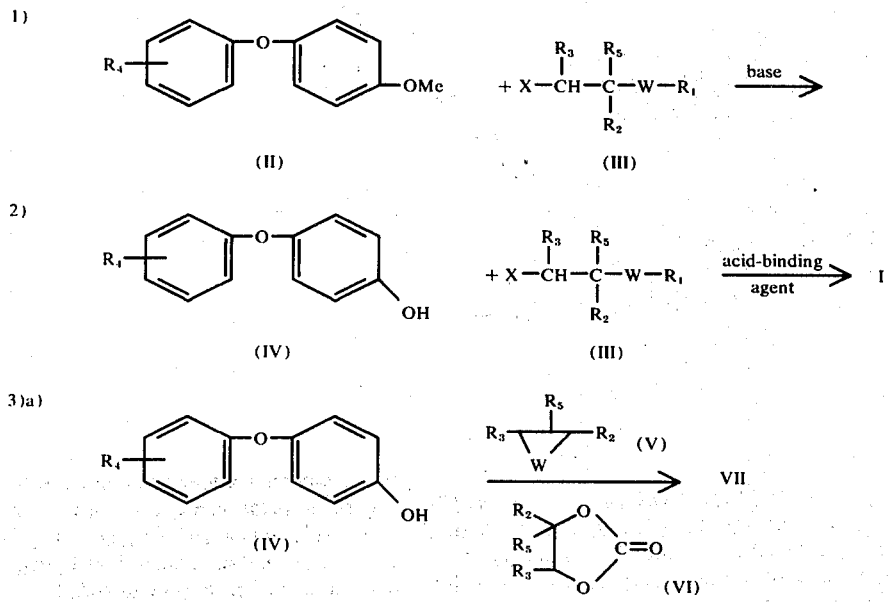

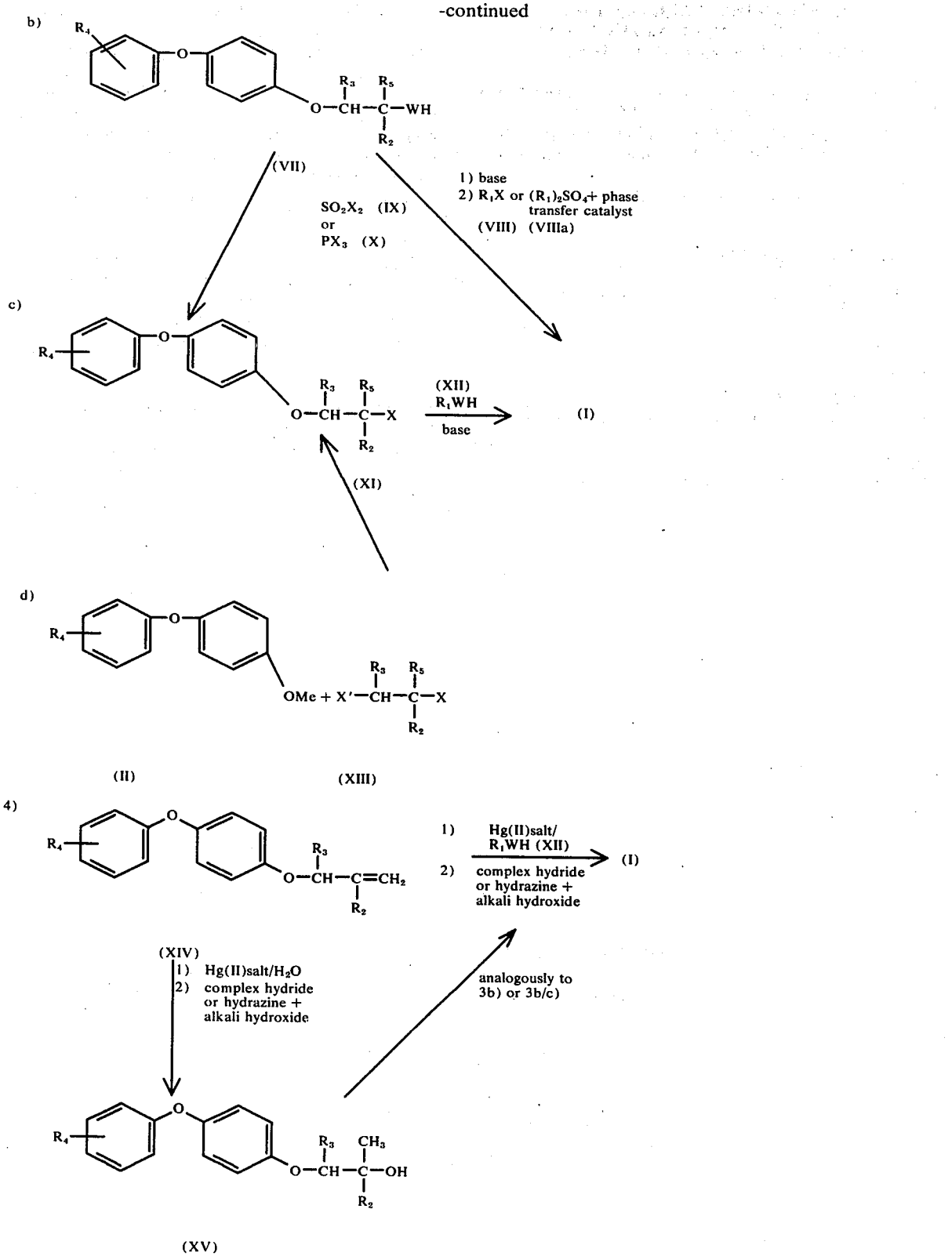

In formulae II to XV, the symbols $R_1$ to $R_5$ and W have the meanings given for formula I; X and X' stand for a halogen atom and Me for a metal, especially for a metal of the 1st and 2nd main group of the periodic system. By phase transfer catalysts are meant tetra-alkylammonium halides, such as tetra-butylammonium iodide or tetra-butylammonium bromide.

Suitable acid-binding agents or bases are, for example, inorganic bases such as hydrides or hydroxides; or alkoxides and carbonates of alkali metals and alkaline-earth metals. The processes 1, 2, 3 and 4 are performed at a reaction temperature of between 0° and 140° C, preferably at between 10° and 110° C, at normal pressure and in the presence of solvents or diluents.

Suitable solvents or diluents are, e.g., dialkyl ethers such as diisopropyl ether; 1,2-dimethoxyethane, dioxane or tetrahydrofuran; N,N-dialkylated carboxylic acid amides such as dimethylformamide; ketones such as acetone, methyl ethyl ketone or cyclohexanone, as well as hexamethylphosphoric acid triamide, dimethyl sulphoxide or sulpholane.

The starting materials of formulae II to VI are known compounds, or they can be produced by methods analogous to known methods described in the literature. Compounds of formula I are suitable for the control of various animal and plant pests. They are particularly suitable for the control of insects of the families: *Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae* and *Pulicidae*, as well as acarids of the *Tetranychidae* family.

The insecticidal and acaricidal action can be appreciably broadened and adapted to suit given circumstances by the addition of other insecticides and/or acaricides. Suitable additives are, for example, the following:
organic phosphorus compounds,
nitrophenols and derivatives thereof,
formamidines,
ureas,
carbamates or chlorinated hydrocarbons,
or pyrethroids.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilizers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:
 solid preparations: dusts, scattering agents, granulates, coated granulates, impregnated granulates and homogeneous granulates;
 liquid preparations:
 a. water-dispersible active-substance concentrates: wettable powders, pastes or emulsions,
 b. solutions.

The content of active substance in the described preparations is between 0.1 and 95%.

The active substances of formula I can be formulated, for example, as follows:

Dusts

The following substances are used to prepare (a) a 5% dust, and (b) a 2% dust:
 a. 5 parts of active substance,
 95 parts of talcum;
 b. 2 parts of active substance,
 1 part of highly dispersed silicic acid,
 97 parts of talcum.
The active substances are mixed and ground with the carriers.

Granulate

The following substances are used to produce a 5% granulate:
 5 parts of active substance,
 0.25 part of epichlorohydrin,
 0.25 part of cetyl polyglycol ether,
 3.50 parts of polyethylene glycol,
 91 parts of kaolin (particle size 0.3–0.8 mm).
The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder

The following constituents are used in the preparation of (a) a 40%, (b) and (c) a 25%, and (d) a 10% wettable powder:
 a. 40 parts of active substance,
 5 parts of sodium lignin sulphonate,
 1 part of sodium dibutyl-naphthalene sulphonate,
 54 parts of silicic acid;
 b. 25 parts of active substance,
 4.5 parts of calcium lignin sulphonate,
 1.9 parts of Champagne chalk/hydroxyethyl cellulose mixture (1:1),
 1.5 parts of sodium dibutyl naphthalene sulphonate,
 19.5 parts of silicic acid
 19.5 parts of Champagne chalk,
 28.1 parts of kaolin;
 c. 25 parts of active substance,
 2.5 parts of isooctylphenoxy-polyoxyethylene-ethanol,
 1.7 parts of Champagne chalk/hydroxyethyl cellulose mixture (1:1),
 8.3 parts of sodium aluminium silicate,
 16.5 parts of kieselgur,
 46 parts of kaolin;
 d. 10 parts of active substance,
 3 parts of a mixture of the sodium salts of saturated fatty alcohol sulphates,
 5 parts of naphthalenesulphonic acid/formaldehyde condensate,
 82 parts of kaolin.
The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates

The following substances are used to produce (a) a 10%, (b) a 25% and (c) a 50% emulsifiable concentrate:
 a. 10 parts of active substance,
 3.4 parts of epoxidised vegetable oil, 3.4 parts of a combination emulsifier consisting of fatty alcohol polyglycol ether and alkylarylsulphonate calcium salt,
40 parts of dimethylformamide,
43.2 parts of xylene;

b. 25 parts of active substance,
2.5 parts of epoxidised vegetable oil,
10 parts of alkylarylsulphonate/fatty alcoholpolyglycol ether mixture,
5 parts of dimethylformamide,
57.5 parts of xylene;

c. 50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of any desired concentration.

Spray

The following constituents are used to prepare a 5% and 95% spray, respectively:
5 parts of active substance,
1 part of epichlorohydrin,
94 parts of ligroin (boiling limits 160°–190° C); and
95 parts of active substance,
5 parts of epichlorohydrin.

EXAMPLE 1

A. Production of 1-phenoxy-4-[2-vinyloxy)-ethoxy]-benzene 20.6 g of finely pulverised anhydrous potassium carbonate and 0.5 g of finely pulverised potassium iodide are added to a solution of 18.6 g of 4-phenoxyphenol in 90 ml of dimethylformamide. An addition is then made dropwise at 60°–65° C in the course of 3 hours, with stirring, of 13.8 g of 2-chloroethyl-vinyl ether, and the reaction mixture is stirred for a further 35 hours at 60°–65° C. The reaction mixture is thereupon poured into 800 ml of ice water and is repeatedly extracted with n-hexane and diethyl ether. The combined organic phases are washed with 10% potassium hydroxide solution and subsequently with saturated sodium chloride solution and dried over sodium sulphate; the solvent is then distilled off. The crude product, which has solidified in crystalline form after removal of the solvent, is crystallised firstly from methanol and afterwards from isopropanol to yield pure 1-phenoxy-4-[(2-vinyloxy)-ethoxy]-benzene, m.p. 51°–52° C.

B. Production of 1-phenoxy-4-(2-methyl-2-propargyloxy)-ethoxy-benzene 3.9 g of an approx. 60% sodium hydride dispersion in mineral oil is washed twice with hexane and once with tetrahydrofuran, and is subsequently covered with 50 ml of tetrahydrofuran and 50 ml of hexamethylphosphoric acid triamide. To this sodium hydride suspension there is then added dropwise at room temperature, within 30 minutes, 24.5 g of 1-phenoxy-4-(2-hydroxy-2-methyl)-ethoxybenzene, dissolved in 50 ml of tetrahydrofuran, and stirring is maintained for a further 5 hours at room temperature. An addition is then made dropwise in the course of 30 minutes, with slight cooling (ice water), of 14 g of propargyl bromide, and the whole is further stirred overnight at room temperature. In further processing, the tetrahydrofuran is extensively removed in vacuo; the residue is poured onto 500 ml of ice water and repeatedly extracted with ether. The combined ether phases are again washed with water and saturated sodium chloride solution, dried over sodium sulphate and thereupon completely freed from ether. The residue is further purified by chromatography on silica gel (eluant: diethyl ether/hexane 1:3) to yield pure 1-phenoxy-4-[(2-methyl-2-propargyloxy)-ethoxy]-benzene ($n_D^{20}$: 1.5569).

The 1-phenoxy-4-(2-hydroxy-2-methyl)-ethoxy-benzene used as starting product is produced as follows: a mixture of 93 g of 4-phenoxy-phenol, 46.5 g of propylene oxide and 2 g of triethylamine is heated in an oil bath in the course of 16 hours, with gradual temperature rise, to a bath temperature of 108° C. After cooling, the reaction mixture is diluted with ether; it is then washed twice with 10% aqueous hydrochloric acid, three times with 10% potassium hydroxide solution and then with saturated sodium chloride solution until neutral. After drying of the ether solution over sodium sulphate, the mixture is completely evaporated by evaporation, and the solidifying residue is recrystallized from hexane/isopropanol (3:1) to obtain pure 1-phenoxy-4-(2-hydroxy-2-methyl)-ethoxy-benzene, m.p. 70°–71° C.

EXAMPLE 2

The solution of 22.6 g of 1-phenoxy-4-allyloxybenzene in 100 ml of absolute ethanol is added dropwise in the course of 40 minutes, with vigorous stirring, to a suspension, cooled to −3° C, of 31.8 g of mercury-(II)-acetate in 200 ml of absolute ethanol. After the addition of the allyloxy compound, the whole is stirred for 5 hours at 22°–25° C. The reaction mixture is subsequently cooled to 0° C and there are then added 125 ml of a 3N aqueous sodium hydroxide solution precooled to 0° C and, immediately afterwards, 125 ml of a 0.5N sodium borohydride solution in 3N sodium hydroxide solution. After addition of the reducing agent, stirring is continued for 14 hours at room temperature. In further processing, the reaction mixture is decanted from the precipitated mercury; the overlying solution is poured into 800 ml of saturated sodium chloride solution, and extraction is performed four times with diethyl ether. The combined ether phases are washed with sodium chloride solution and dried over sodium sulphate; the solvent is then completely removed in vacuo. The oily residue is further purified by chromatography on silica gel (eluant: diethyl ether/hexane 1:4) to obtain pure 1-phenoxy-4-[(2-ethoxy-2-methyl)-ethoxy]-benzene ($n_D^{20}$: 1.5420).

The following compounds are produced in an analogous manner:

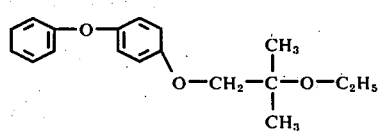

$n_D^{20}$: 1,5382

-continued
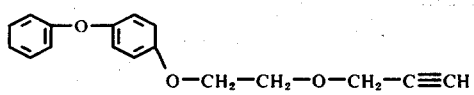
m.p.: 33–35° C
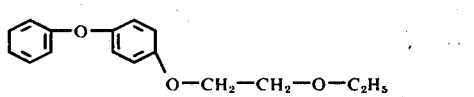
$n_D^{20}$: 1,5514
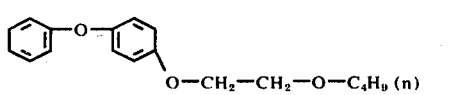
$n_D^{20}$: 1,5432
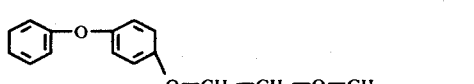
m.p.: 30–32° C
$n_D^{20}$: 1,5483
$n_D^{20}$: 1,5298
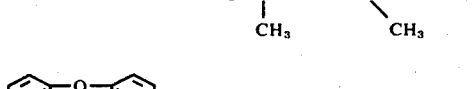
$n_D^{20}$: 1,5431
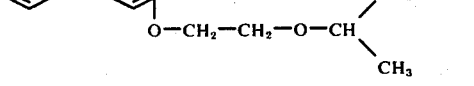
$n_D^{20}$: 1,5552
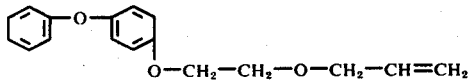
$n_D^{20}$: 1,5743
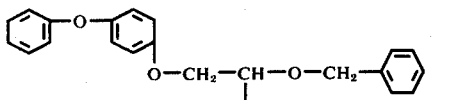
$n_D^{20}$: 1,6087
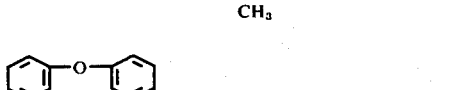
$n_D^{20}$: 1,5471
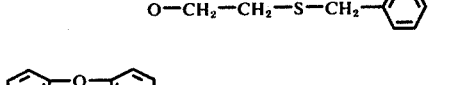
$n_D^{20}$: 1,5628
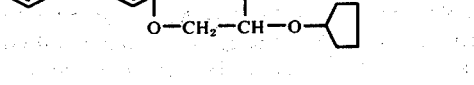
m.p.: 30–32° C
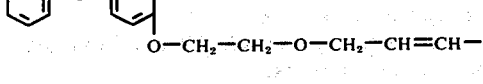
$n_D^{20}$: 1,5536
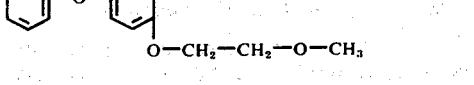
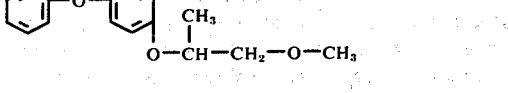

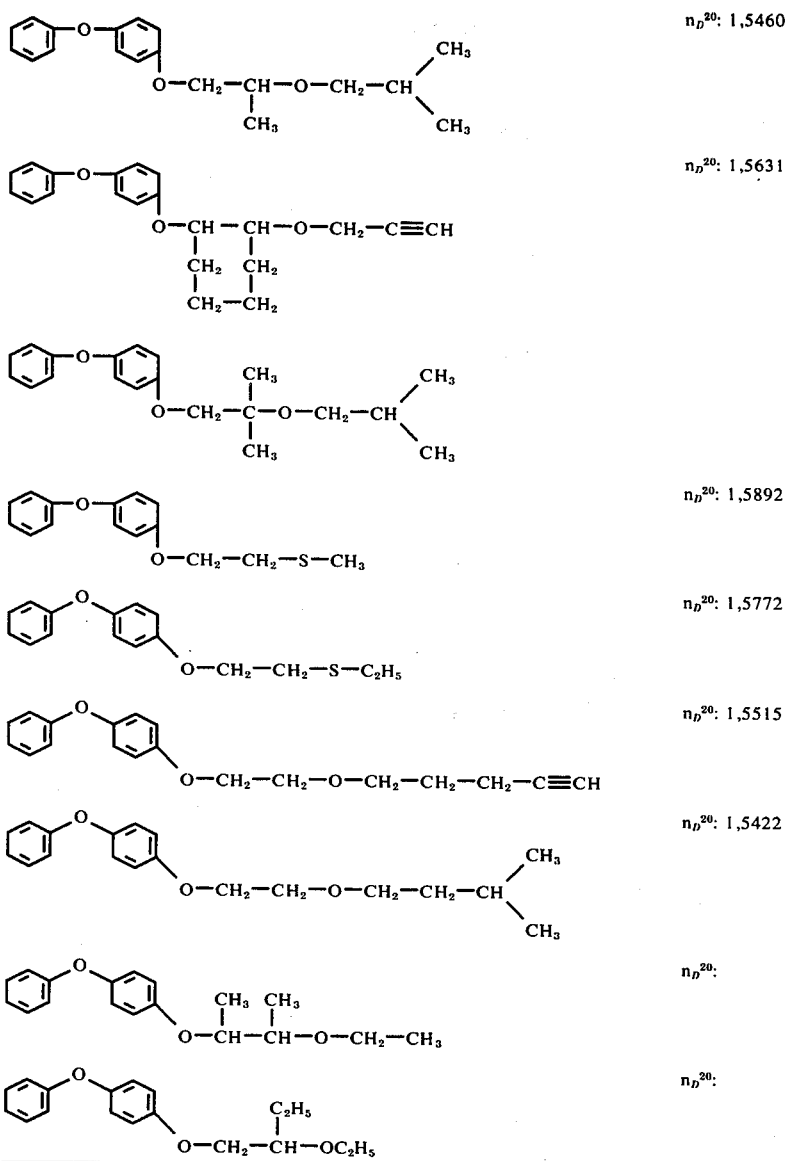

EXAMPLE 3

A. Contact action on *Dysdercus-fasciatus* larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of *Dysdercus fasciatus* were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Example 1 exhibited a good action in the above test.

B. Contact action on *Aëdes-aegypti* larvae

About 20 two-day-old larvae of the yellow-fever mosquito (*Aëdes aegypti*) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

Compounds according to EXAMPLE 1 exhibited a good action in the above test.

C. Contact action on *Tenebrio-molitor* pupae

A specific amount of a 0.1% acetonic active-substance solution corresponding to 10 mg of active substance per square metre was transferred by pipet into an aluminium dish and uniformly distributed. After evaporation of the acetone, 10 freshly formed pupae were placed onto the treated surface, and the dish was covered with a perforated lid. After the control insects had left the cocoon as imagines, the test insects were examined to determine the number of normal adults.

Compounds according to EXAMPLE 1 exhibited a good action in the above test.

EXAMPLE 4

A. Action against *Musca domestica*

An amount in each case of 50 g of CSMA maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate off. There were then deposited per active substance in each case 25 one-, two- or three-day-old maggots and about 50 fly eggs. After completion of pupation, the pupae were flushed out and counted. After a period of ten days, the number of emerged flies was counted and hence any effect on metamorphosis was established.

Compounds according to EXAMPLE 1 exhibited in this test a good action against *Musca domestica*.

B. Action against *Ephestia kühniella*

50 g of wheat flour was made up in two beakers with a specific amount of active substance to give a 5% dust, the concentration being 0.05%. Into each beaker (25 g of flour) there were placed 10 larvae of *Ephestia kühniella*. The pattern of population was ascertained over a period of 8 weeks and the number of moths determined.

Compounds according to EXAMPLE 1 exhibited a good action in this test against *Ephestia kühniella*.

EXAMPLE 5

Action against red spider mites

*Phaseolus vulgaris* (bush beans) were infested, 12 hours before the test for acaricidal action, with an infested piece of leaf from a mass culture of Tetranychus urticae. The transferred mobile stages were sprayed with the emulsified test preparations, at a concentration of 0.04%, by means of a chromatography-sprayer in a manner ensuring no running-off of the spray liquor. An assessment was made after 2 to 7 days, by examination under a binocular, of the living and of the dead larvae, adults and eggs, and the results were expressed in percentages. The treated plants were kept during the holding time in greenhouse compartments at 25° C.

Compounds according to EXAMPLE 1 exhibited in the above test a good action against eggs, larvae and adults of *Tetranychus urticae*.

We claim:

1. A compound of the formula

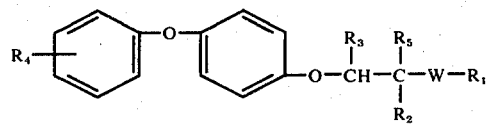

wherein
W represents —S—,
$R_1$ represents $C_1$–$C_6$-alkyl, $C_3$–$C_6$-cycloalkyl or $C_5$–$C_6$-cycloalkenyl, $C_2$–$C_4$-haloalkenyl, $C_3$–$C_5$-alkynyl, $C_2$–$C_4$-alkenyl or benzyl,
$R_2$ represents hydrogen, methyl or ethyl,
$R_3$ represents hydrogen or methyl, or
$R_2$ and $R_3$ together with the chain represent a 5- or 6-membered saturated ring, and
$R_4$ and $R_5$ each represent hydrogen or methyl.

2. A compound according to claim 1 wherein
$R_1$ represents $C_1$–$C_6$-alkyl, $C_3$–$C_6$-cycloalkyl, $C_3$–$C_4$-alkynyl, $C_2$–$C_4$-alkenyl or $C_3$–$C_4$-chloroalkenyl,
$R_2$ represents hydrogen or methyl, and
$R_3$, $R_4$ and $R_5$ each represent hydrogen.

* * * * *